United States Patent
Raje et al.

(10) Patent No.: US 9,351,436 B2
(45) Date of Patent: May 24, 2016

(54) STUD BUMP BONDING IN IMPLANTABLE MEDICAL DEVICES

(71) Applicants: Milind Raje, Wentworthville (AU); Robert Bennett, St. Peters (AU); Andrew Mudie, Petersham (AU); Gary Mark Ignacio, Woolloomooloo (AU)

(72) Inventors: Milind Raje, Wentworthville (AU); Robert Bennett, St. Peters (AU); Andrew Mudie, Petersham (AU); Gary Mark Ignacio, Woolloomooloo (AU)

(73) Assignee: Cochlear Limited, Macquarie University, NSW (AU)

( * ) Notice: Subject to any disclaimer, the term of this patent is extended or adjusted under 35 U.S.C. 154(b) by 575 days.

(21) Appl. No.: 13/790,141

(22) Filed: Mar. 8, 2013

(65) Prior Publication Data
US 2014/0254124 A1 Sep. 11, 2014

(51) Int. Cl.
| | | |
|---|---|---|
| B23K 1/06 | (2006.01) | |
| B23K 26/00 | (2014.01) | |
| H05K 13/04 | (2006.01) | |
| B23K 20/00 | (2006.01) | |
| A61N 1/375 | (2006.01) | |
| H05K 3/34 | (2006.01) | |
| H05K 3/40 | (2006.01) | |
| A61N 1/36 | (2006.01) | |

(52) U.S. Cl.
CPC .......... *H05K 13/0465* (2013.01); *A61N 1/3754* (2013.01); *B23K 1/06* (2013.01); *B23K 20/004* (2013.01); *B23K 26/21* (2015.10); *H05K 3/4015* (2013.01); *A61N 1/36032* (2013.01); *H01L 2924/0002* (2013.01); *H05K 3/3478* (2013.01); *H05K 3/4007* (2013.01); *H05K 2201/0379* (2013.01); *H05K 2201/0979* (2013.01); *H05K 2201/10318* (2013.01); *H05K 2203/0285* (2013.01); *H05K 2203/049* (2013.01); *H05K 2203/107* (2013.01)

(58) Field of Classification Search
None
See application file for complete search history.

(56) References Cited

U.S. PATENT DOCUMENTS

| | | | |
|---|---|---|---|
| 4,750,666 A | | 6/1988 | Neugebauer et al. |
| 5,186,381 A | * | 2/1993 | Kim ................... H01L 24/11 228/123.1 |
| 5,945,065 A | * | 8/1999 | Kikuchi ................ C22C 5/02 228/262.2 |
| 5,976,964 A | | 11/1999 | Ball |
| 6,001,724 A | * | 12/1999 | Stansbury ............ H01L 24/11 228/180.5 |
| 6,031,710 A | | 2/2000 | Wolf et al. |
| 6,414,835 B1 | | 7/2002 | Wolf et al. |
| 6,492,737 B1 | * | 12/2002 | Imasu .................. H01L 21/563 257/723 |
| 6,660,626 B1 | | 12/2003 | Lin |
| 6,845,664 B1 | | 1/2005 | Okojie |
| 6,920,673 B2 | | 7/2005 | Allen et al. |

(Continued)

FOREIGN PATENT DOCUMENTS

EP 1030357 A1 8/2000

OTHER PUBLICATIONS

Jim Ohneck, "What universities aren't teaching students," retrieved from http://www.medicaldesign.com/electrical-components/universities_arent_teaching_students_0309/index.html, on Nov. 28, 2012, pp. 1-2.

*Primary Examiner* — Kiley Stoner
(74) *Attorney, Agent, or Firm* — Edell, Shapiro & Finnan, LLC

(57) ABSTRACT

Presented herein are stud bump bonding techniques for electrically connecting an elongate conductor, such as a wire or pin, to a bonding pad. A plurality of stud bumps are bonded to a surface of a bonding pad and an elongate electrical conductor is positioned in proximity to the plurality of stud bumps. The elongate conductor is bonded to one or more of the stud bumps.

14 Claims, 12 Drawing Sheets

(56) References Cited

U.S. PATENT DOCUMENTS

| | | |
|---|---|---|
| 6,985,347 B2 | 1/2006 | Stevenson et al. |
| 7,046,499 B1 | 5/2006 | Imani et al. |
| 7,180,318 B1 | 2/2007 | Mahoney et al. |
| 7,260,434 B1 | 8/2007 | Lim et al. |
| 7,408,243 B2 | 8/2008 | Shiffer |
| 8,121,697 B2 | 2/2012 | Greenberg et al. |
| 8,131,369 B2 | 3/2012 | Taylor et al. |
| 8,165,680 B2 | 4/2012 | Greenberg et al. |
| 2004/0049239 A1* | 3/2004 | Swanson .............. A61N 1/3754 607/36 |
| 2004/0201947 A1* | 10/2004 | Stevenson ............ A61N 1/3752 361/302 |
| 2005/0007718 A1* | 1/2005 | Stevenson ............ A61N 1/3754 361/118 |
| 2006/0043995 A1* | 3/2006 | Williams ............ G01R 1/06716 324/755.07 |
| 2006/0125501 A1* | 6/2006 | Liu .................... G01R 31/2889 324/750.25 |
| 2007/0043399 A1 | 2/2007 | Stevenson et al. |
| 2007/0164378 A1* | 7/2007 | MacGugan ........... B81C 1/0023 257/416 |
| 2007/0207605 A1* | 9/2007 | Shiu .................... H01L 21/4853 438/613 |
| 2008/0119906 A1* | 5/2008 | Starke ................. A61N 1/3754 607/36 |
| 2009/0057866 A1* | 3/2009 | Chow .................. H01L 23/055 257/690 |
| 2009/0116167 A1* | 5/2009 | Stevenson ................ A61N 1/37 361/306.1 |
| 2009/0189261 A1 | 7/2009 | Lim et al. |
| 2009/0240314 A1 | 9/2009 | Kong et al. |
| 2010/0033559 A1 | 2/2010 | Yasunaga |
| 2010/0092795 A1* | 4/2010 | Eskridge .............. B23K 20/007 428/594 |
| 2010/0102444 A1* | 4/2010 | Khor .................... H01L 21/561 257/737 |
| 2010/0225434 A1 | 9/2010 | Wang et al. |
| 2010/0274313 A1* | 10/2010 | Boling ................. A61N 1/0546 607/46 |
| 2010/0308443 A1* | 12/2010 | Suthiwongsunthorn  H01L 21/561 257/621 |
| 2011/0111562 A1 | 5/2011 | San Antonio et al. |
| 2011/0253430 A1* | 10/2011 | Woychik ................ H01L 24/03 174/257 |
| 2011/0270067 A1 | 11/2011 | Faraji et al. |
| 2011/0284284 A1 | 11/2011 | Talamine et al. |
| 2011/0297439 A1 | 12/2011 | Talamine et al. |
| 2012/0155044 A1 | 6/2012 | Shaddock et al. |
| 2012/0205801 A1* | 8/2012 | Bindrup .................. H01L 23/57 257/738 |
| 2013/0070423 A1* | 3/2013 | Iyer ........................ H01R 24/68 361/728 |
| 2014/0209928 A1* | 7/2014 | Teng .................... H01L 25/0753 257/82 |
| 2015/0005573 A1* | 1/2015 | Lehmann ............... A61N 1/025 600/25 |
| 2015/0216051 A1* | 7/2015 | Shah ................... H05K 3/4046 174/262 |

* cited by examiner

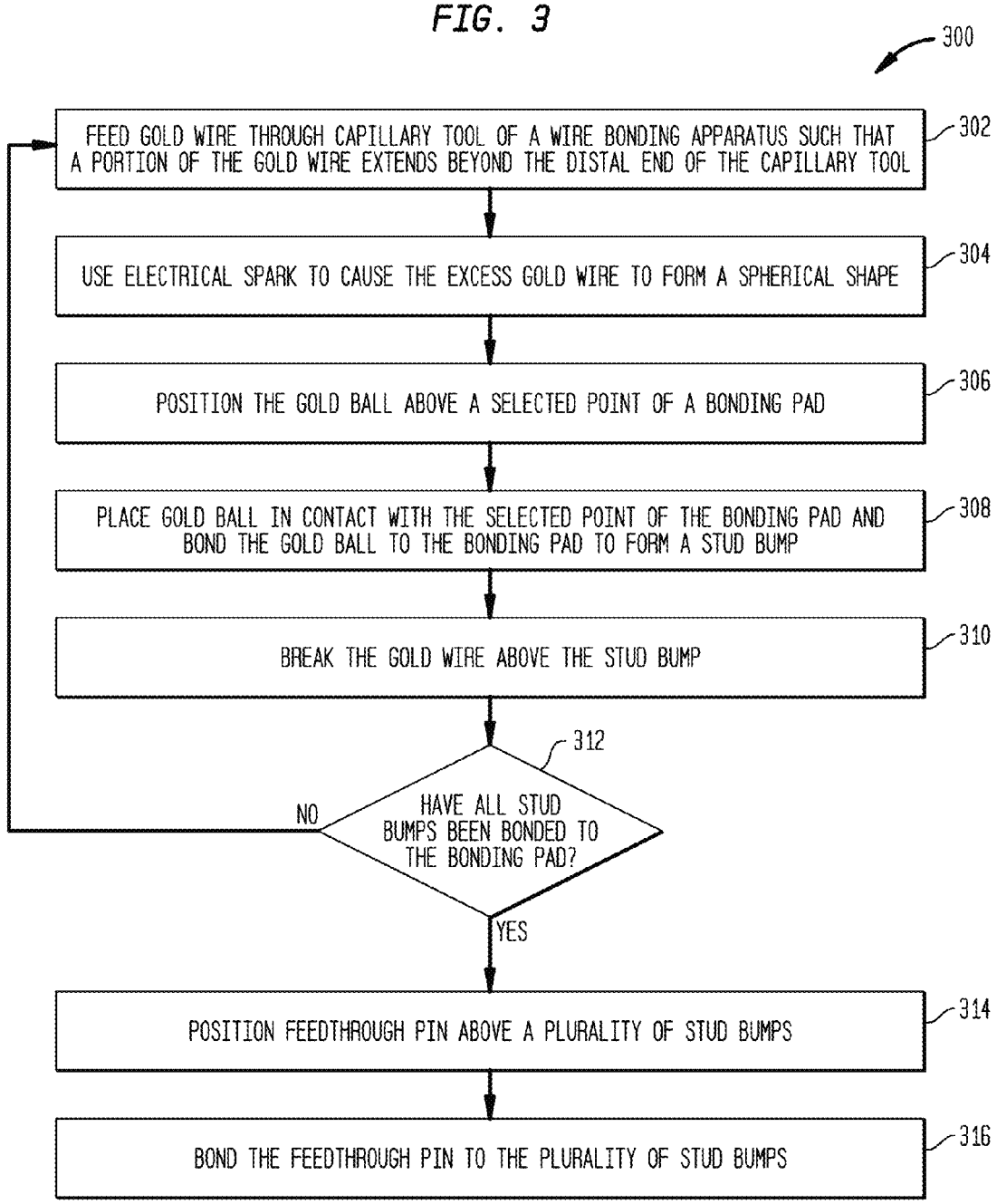

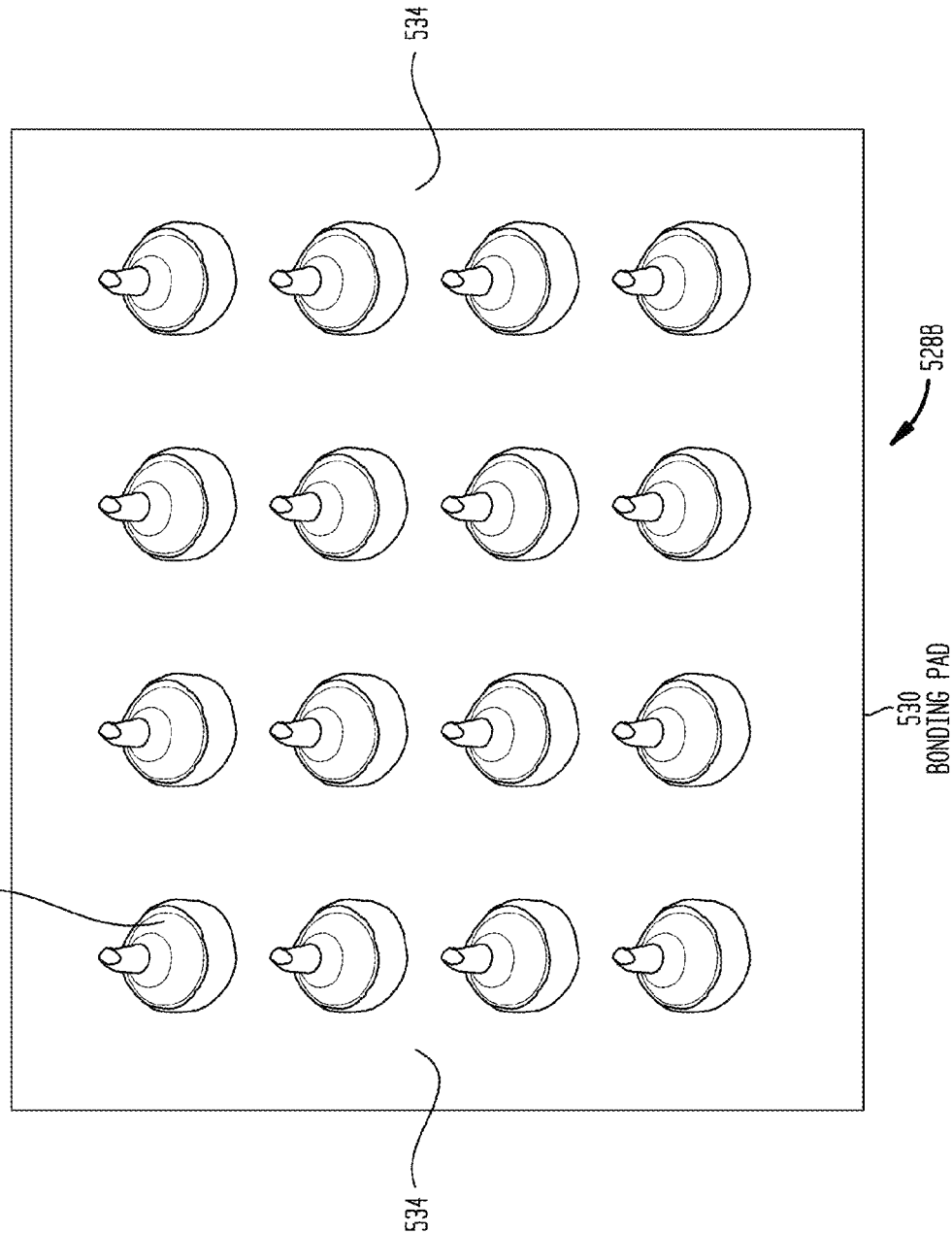

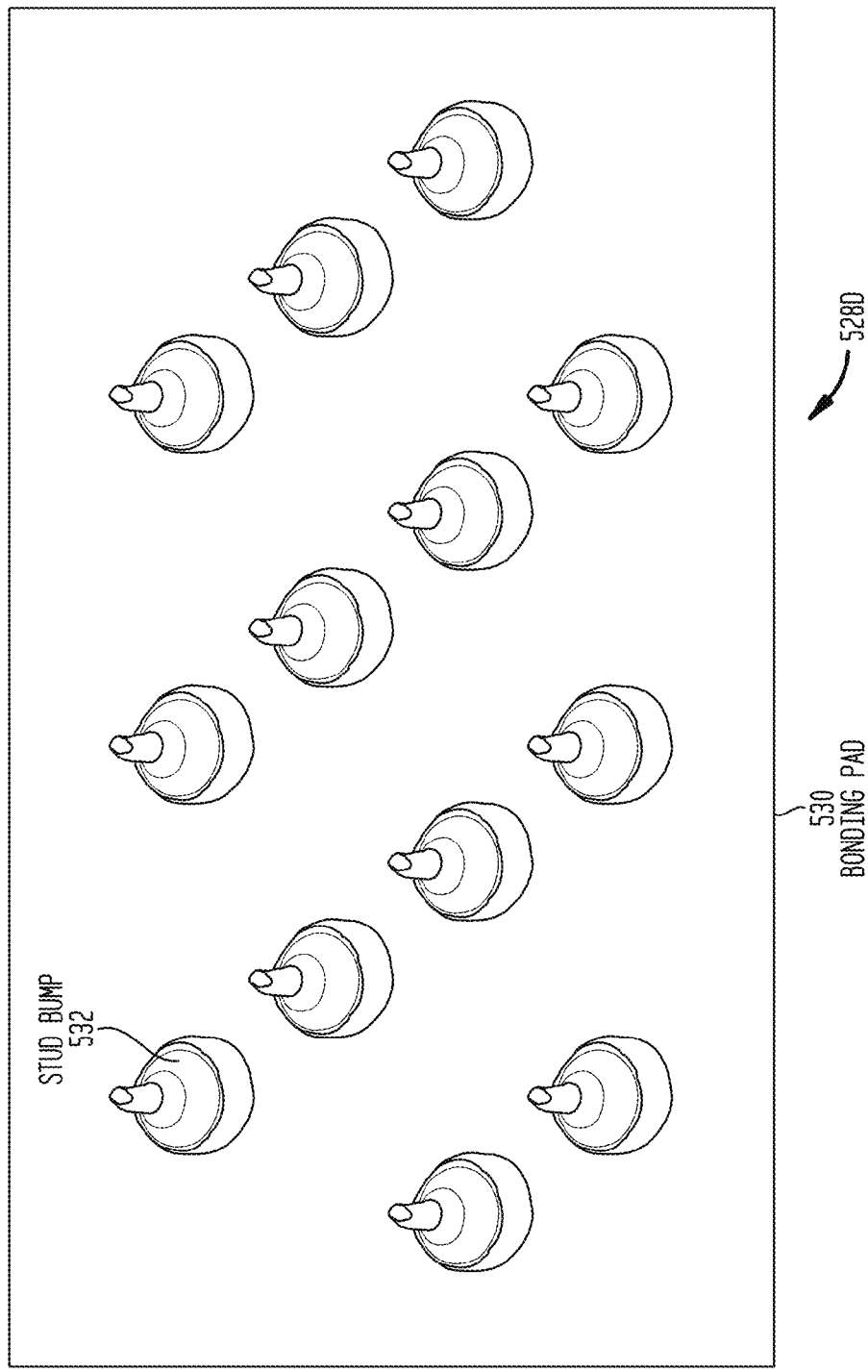

STUD BUMP BONDING IN IMPLANTABLE MEDICAL DEVICES

BACKGROUND

1. Field of the Invention

The present invention relates generally to implantable medical devices, and more particularly, to stud bump bonding in implantable medical devices.

2. Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing life saving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify of the anatomy or of a physiological process.

SUMMARY

In one aspect of the invention, a method is provided. The method comprises bonding a plurality of stud bumps to a surface of a bonding pad of an electronics assembly positioned within a hermetically sealable implantable housing, wherein a hermetic feedthrough comprising a plurality of feedthrough pins extends through the implantable housing. The method further comprises positioning a first feedthrough pin in proximity to the plurality of stud bumps, and bonding the first feedthrough pin to one or more of the stud bumps.

In another aspect of the present invention, a method is provided. The method comprises bonding a plurality of stud bumps to a surface of a bonding pad, positioning an elongate conductor in proximity to the plurality of stud bumps, and bonding the elongate conductor to one or more of the stud bumps. The stud bumps collectively have a sufficient footprint and mass to function as a thermal energy (e.g., heat) sink for heat based joining methods such as laser welding and as a ductile medium for mechanical bonding of the elongate conductor to the one or more stud bumps.

In another aspect of the present invention, an implantable medical device is provided. The implantable medical device comprises a hermetically sealed biocompatible housing, an electronics assembly positioned in the housing and comprising a bonding pad with a plurality of stud bumps disposed thereon, and a hermetic feedthrough extending through the housing and comprising a feedthrough pin. A first end of the feedthrough pin is bonded to one or more of the stud bumps.

BRIEF DESCRIPTION OF THE DRAWINGS

Embodiments of the present invention are described herein in conjunction with the accompanying drawings, in which:

FIG. 3 is a detailed flowchart of a method in accordance with embodiments of the present invention;

FIGS. 5A-5D are perspective views of bonding pads having different arrangements of stud bumps in accordance with embodiments of the present invention;

DETAILED DESCRIPTION

Presented herein are stud bump bonding techniques for electrically connecting an elongate conductor, such as a wire or pin, to a bonding pad. More specifically, in embodiments of the present invention a plurality of stud bumps are first bonded to a surface of a bonding pad. An elongate electrical conductor is then positioned in proximity to the plurality of stud bumps and the elongate conductor is bonded to one or more of the stud bumps.

The stud bump bonding techniques presented herein may be used in implantable medical devices to electrically connect conductors, such as wires or feedthrough pins, to bonding pads. There are many different types of implantable medical devices having a wide variety of corresponding implantable components that may be partially or fully implanted into a recipient. For example, implantable medical devices may include hearing prostheses (e.g., auditory brain stimulators, bone conduction devices, mechanical stimulators, cochlear implants, etc.), sensors, implantable pacemakers, defibrillators, functional electrical stimulation devices, catheters, etc. It is to be appreciated that the stud bump bonding techniques presented herein may be used in connection with any of the above or other implantable medical devices. However, merely for ease of description, the stud bump bonding techniques presented herein are primarily described herein in connection with one exemplary implantable medical device, namely a cochlear implant (also commonly referred to as cochlear implant device, cochlear prosthesis, and the like; simply "cochlear implant" herein).

Figure 1:
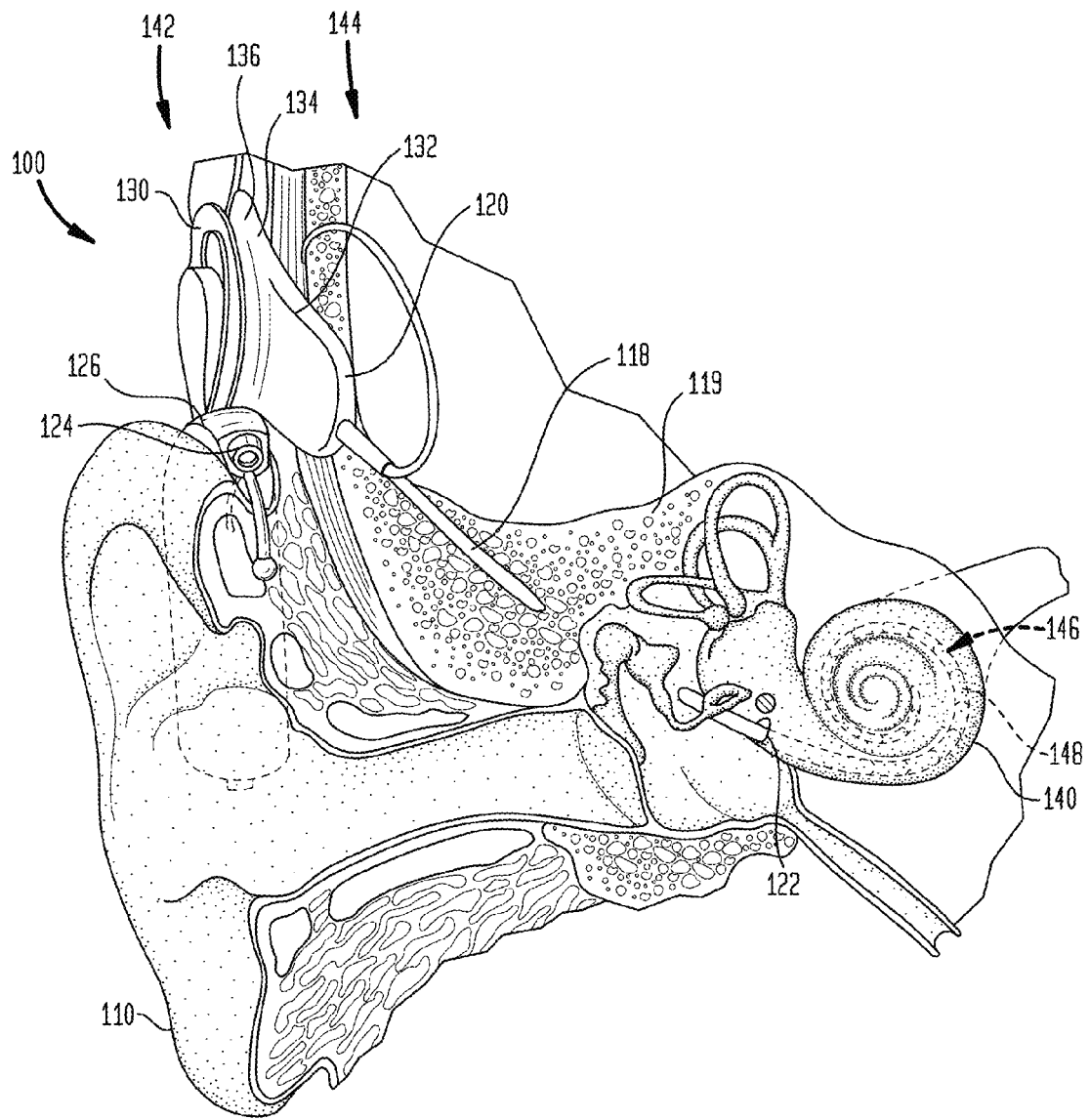
FIG. 1 is a schematic diagram of a cochlear implant having feedthrough pins electrically connected to implant electronics via a stud bump bonding process in accordance with embodiments of the present invention.

FIG. 1 is perspective view of an exemplary cochlear implant 100 in which feedthrough wires are connected to bonding pads of an electronics assembly using the stud bump bonding techniques presented herein. In this embodiment, cochlear implant 100 comprises an external component 142 and an internal or implantable component 144. The external component 142 is directly or indirectly attached to the body of the recipient and typically comprises one or more sound input elements 124 (e.g., microphones, telecoils, etc.) for detecting sound, a sound processor 126, a power source (not shown), an external coil 130 and, generally, a magnet (not shown) fixed relative to the external coil 130. The sound processor 126 processes electrical signals generated by a sound input element 124 that is positioned, in the depicted embodiment, by auricle 110 of the recipient. The sound processor 126 provides the processed signals to external coil 130 via a cable (not shown).

The internal component 144 comprises an elongate stimulating assembly 118, a stimulator unit 120, and an internal receiver/transceiver unit 132, sometimes referred to herein as transceiver unit 132. The transceiver unit 132 is connected to an internal coil 136 and, generally, a magnet (not shown) fixed relative to the internal coil 136. Internal transceiver unit 132 and stimulator unit 120 are sometimes collectively referred to herein as a stimulator/transceiver unit.

The magnets in the external component 142 and internal component 144 facilitate the operational alignment of the external coil 130 with the internal coil 136. The operational alignment of the coils enables the internal coil 136 to transmit/receive power and data to/from the external coil 130. More specifically, in certain examples, external coil 130 transmits electrical signals (e.g., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding 134. In use, transceiver unit 132 may be positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

Elongate stimulating assembly 118 has a proximal end connected to the stimulator unit 120 and a distal end implanted in cochlea 140. Elongate stimulating assembly 118 also includes a contact array 146 that comprises a plurality of stimulating contacts 148 that may be electrical and/or optical contacts. Stimulating assembly 118 extends from stimulator unit 120 to cochlea 140 through mastoid bone 119 and a cochleostomy 122.

Figure 2:
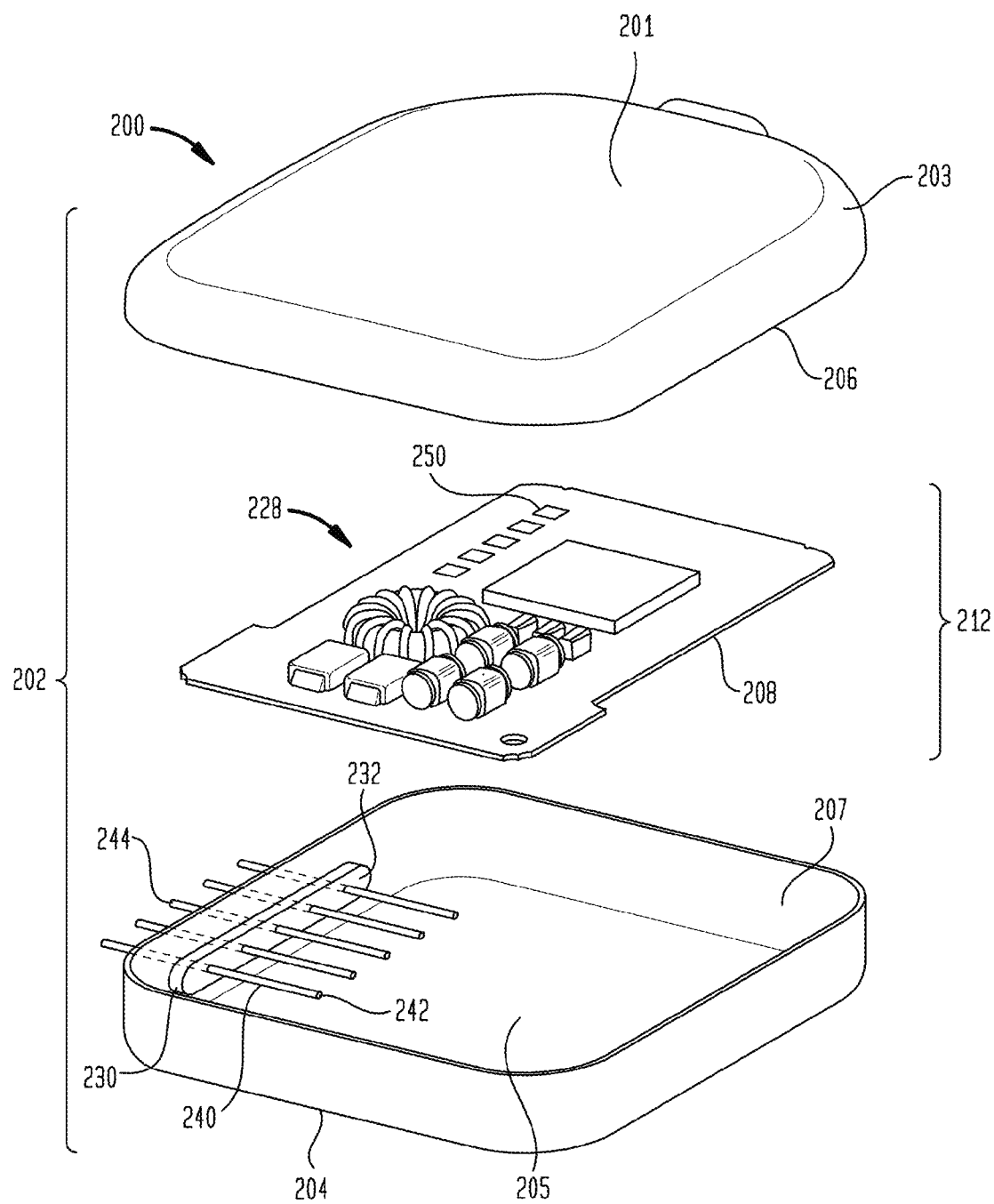
FIG. 2 is an exploded view of a portion of an implantable component of an implantable medical device in accordance with embodiments of the present invention.

FIG. 2 is an exploded perspective view of a portion of an implantable component 200 of an example implantable medical device, namely a cochlear implant, in accordance with embodiments of the present invention. Implantable component 200 comprises a hermetically-sealed housing/enclosure in the form of container 202. Hermetically-sealed container 202 is formed by a bottom shell 204 hermetically sealed to a top shell 206. Container 202 defines a hermetic enclosure in which an electronics assembly 212 is located. In the embodiment illustrated in FIG. 2, electronics assembly 212 includes a printed circuit board (PCB) 208 and electronic components (implant electronics) 228 mounted on the PCB 208.

Top shell 206 comprises a lateral surface 201 defining the top surface of the container 202 and side walls 203 extending generally orthogonally from the lateral surface. Similarly, bottom shell 204 comprises a lateral surface 205 defining the bottom surface of the container 202 and side walls 207 extending generally orthogonally from the lateral surface. It should be appreciated, however, that top shell 206 and bottom shell 204 can be coupled in a myriad of different ways. In one example, top shell 206 and bottom shell 204 are configured to directly mate with each other at the edges of walls 203 and 207. The shells 204 and 206 can be formed of a suitable biocompatible material such as titanium, stainless steel or cobalt-chromium alloys, and can be joined using techniques such as laser welding or diffusion bonding.

Container 202 further comprises a hermetic feedthrough 230 disposed in a wall 207 of bottom shell 204. In the embodiment illustrated in FIG. 2, feedthrough 230 includes an insulating body 232 disposed in an aperture (not shown) of wall 207. The insulating body 232 is attached to the wall 207 to form a hermetic seal. Additionally, a plurality of electrical conductors, referred to as feedthrough wires or pins 240, extend through the insulating body 232. The feedthrough pins 240 each have a first end 242 that extends inside of the bottom shell 204 (i.e., positioned within the container 202) and a second end 242 that extends outside of the bottom shell (i.e., positioned external to the container 202). As such, the feedthrough pins 240 are configured to provide electrically conductive paths (e.g., electrical input/output lines) between components inside and outside of the hermetic enclosure of container 202, without degrading the hermetic seal of the enclosure. That is, the feedthrough 230 provides electrical connections between the electronics assembly 212 within the hermetically sealed container 202, while protecting the electronics assembly from any damage or malfunction that may result from exposure to the surrounding environment. In the example of FIG. 2, the feedthrough pins 240 are platinum pins.

FIG. 2 illustrates an example where the feedthrough 230 includes five feedthrough pins 240. It is to appreciated that the use of five feedthrough pins is merely illustrative and that alternative hermetic feedthroughs may include more or fewer conductors to provide electrical connections through container 202.

In the embodiment illustrated in FIG. 2, second ends 244 of feedthrough pins 240 outside of the hermetic enclosure may be electrically connected to different functional components of an implantable medical device. For example, in a cochlear implant, second ends 244 of feedthrough pins 240 may be electrically connected to an internal transcutaneous transfer coil, stimulating contacts, etc. Additionally, the first ends 242 of feedthrough pins 240 are each configured to be electrically connected to electronics assembly 212. More specifically, the first ends 242 of feedthrough pins 240 are each configured to be bonded to a respective bonding pad 250 on PCB 208. In accordance with embodiments of the present invention, the first ends 242 of feedthrough pins 240 are bonded to the bonding pads 250 through a stud bump bonding method/process.

FIG. 3 is a flowchart of an example stud bumping method 300 for attaching a feedthrough pin to a bonding pad in accordance with embodiments of the present invention. For ease of illustration, the method 300 of FIG. 3 will be described with reference to the schematic diagrams of FIGS. 4A-4F.

Figure 4A:
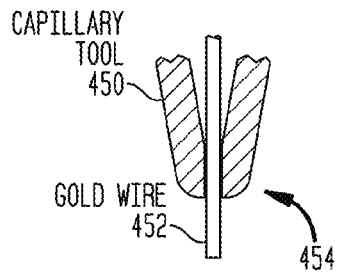
FIGS. 4A-4F are schematic diagrams illustrating steps of a stud bump bonding process in accordance with embodiments of the present invention.

Method 300 begins at step 302 where a wire 452 (FIG. 4A) is fed through a capillary tool 450 (FIG. 4A) of a wire bonding apparatus. As shown in FIG. 4A, the wire 452 is a gold wire that extends beyond a distal end 454 of the capillary tool 450.

Figure 4B:
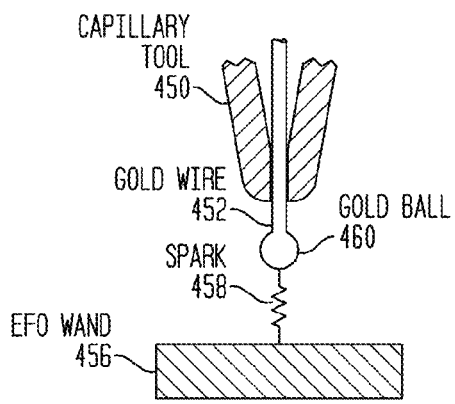

At step 304 of FIG. 3, a high voltage electric charge is used to melt the end of the gold wire 452 into a spherical or ball shape. More specifically, as shown in FIG. 4B, an Electrical Flame Off (EFO) wand 456 generates a spark 458 that causes the end of the gold wire 452 to form into a free air gold ball 460. In general, the gold ball 460 may be larger than the opening in the capillary tool 450 through which the gold wire 452 is fed.

Figure 4C:
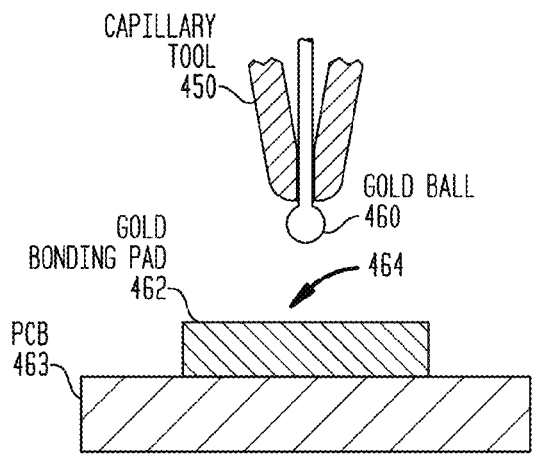

At step 306 of FIG. 3, the capillary tool 450 and gold ball 460 are positioned above a selected point 464 of a bonding pad 462 (FIG. 4C). The bonding pad 462 may be, for example, a gold bonding pad (e.g., a bonding pad having a gold surface)

disposed on a PCB 463. The PCB may be clamped securely to a heated workstage so that the bonding pad 462 may also be heated at step 306.

Figure 4D:
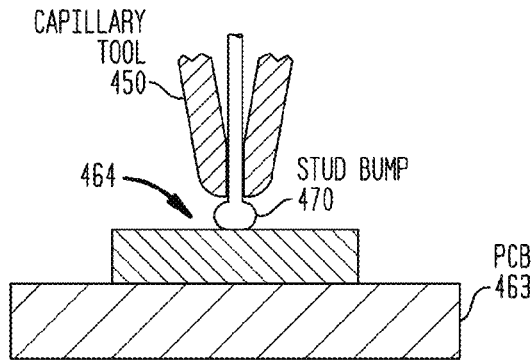

At step 308 of FIG. 3, the capillary tool 450 is moved so that the gold ball 460 is placed in contact with the selected point 464. As shown in FIG. 4D, one or more of energy, heat, pressure, and/or vibration is used to bond the gold ball 460 with the gold bonding pad 462 at the selected point 464, thereby creating a gold stud bump 470. That is, a gold-to-gold bond is formed that results in a protrusion (referred to as a stud bump) that disposed on the surface of the bonding pad 462.

In one specific embodiment, the gold ball 460 is pushed onto the bonding pad 462 at preselected location 464 and ultrasonic power is applied for a set period, typically a few milliseconds. The heat (applied to the bonding pad 462 via a heated work stage), ultrasonic power, and pressure causes the gold ball 460 to rub on the bonding pad 462 and form a bond.

Figure 4E:
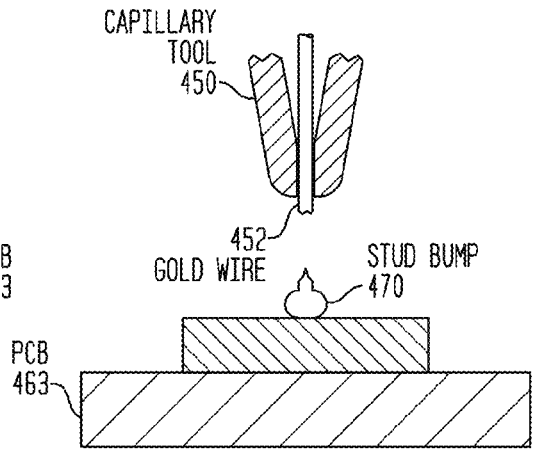

At step 310, the capillary tool 450 is lifted and moved sideways to break the gold wire 452 above the stud bump 470. As shown in FIG. 4E, the stud bump 470, and possible a slight wire tail, remains on the bonding pad 462. In general, the steps 302-310 collectively comprise a wire bonding process that results in the formation of stud bump 470.

In general, a plurality of stud bumps will be bonded to the bonding pad 462. As such, a determination is made at step 312 as to whether all desired stud bumps have been bonded to the bonding pad 462. If all of the desired stud bumps have not been bonded to the bonding pad 462, steps 302-310 are repeated until the desired number of stud bumps have been formed.

Figure 4F:
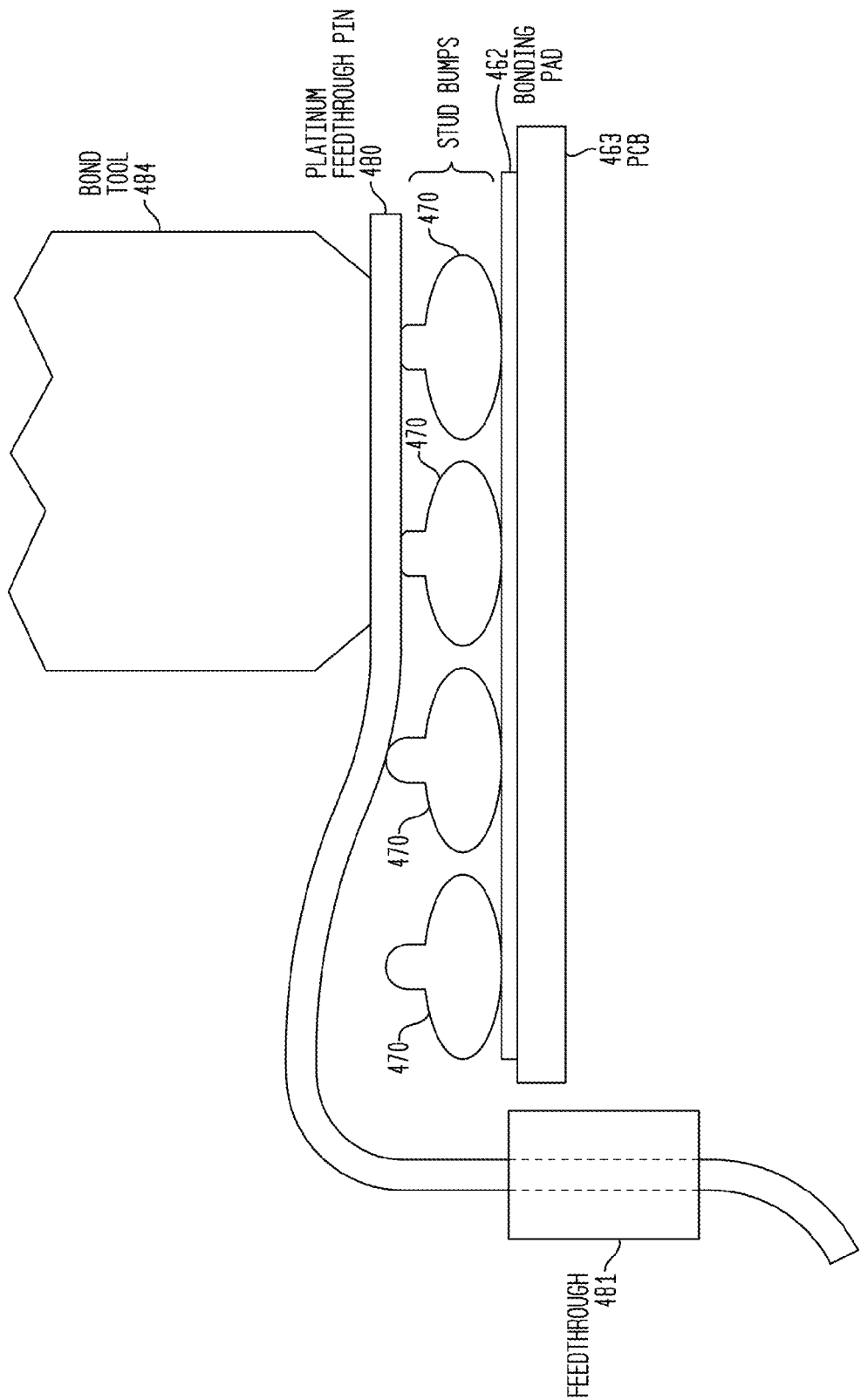
Figure 4G:
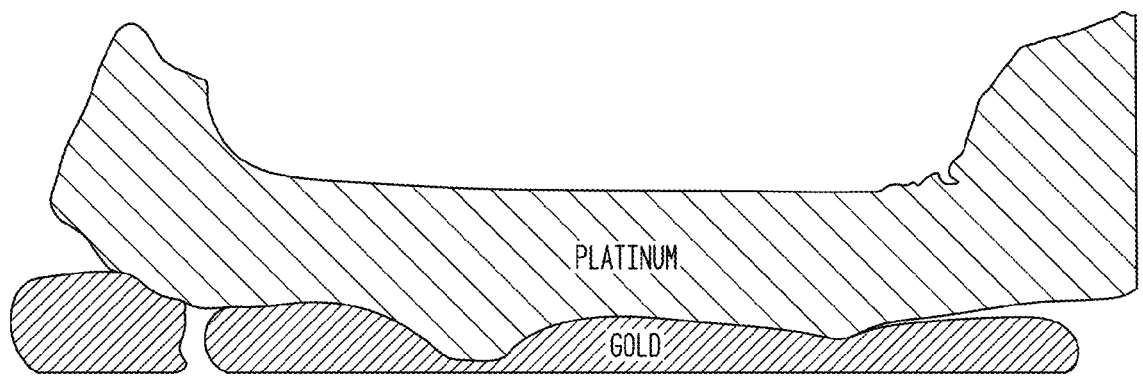
FIG. 4G is a cross-sectional view of a platinum feedthrough pin bonded to a bonding pad in accordance with embodiments of the present invention.

If, at step 312, it is determined that all of the desired stud bumps have been formed, then method 300 proceeds to step 314 where a feedthrough pin 480 (FIG. 4F) that extends from a feedthrough 481 is positioned above the bonding pad 462. In the example of FIG. 4F, the feedthrough pin 480 is a platinum feedthrough pin. At step 316, a bond tool 484 is used to place the feedthrough pin 480 in contact with a plurality of stud bumps 470 (i.e., to bend the pin towards the pad) and to bond the feedthrough pin 480 to the plurality of stud bumps 470. FIG. 4G is a cross-sectional view of a platinum feedthrough pin, such as pin 480, after bonding to a plurality of gold stud bumps, such as bumps 470.

It is to be appreciated that the feedthrough pin 480 may be bonded to the stud bumps 470 in a number of different manners. Exemplary bonding methods include, but are not limited to, compression bonding, thermo-compression bonding, ultrasonic bonding, thermosonic bonding, laser welding, resistance welding etc. In general, the bonding techniques may use any combination of pressure, heat and ultrasonic energy.

In one specific embodiment, a high powered ultrasonic bonder, (e.g., Wedge bonder, Tape Automated Bonding (TAB) machine, Heavy aluminum bonder, etc.) is used to position an ultrasonic bond tool 484 over the platinum feedthrough pin 480 and gold stud bumps 470. The ultrasonic bond tool 484 uses high levels of ultrasonic energy and heavy pressure to rub the platinum pin 280 against the gold stud bumps 470 and create a contaminant free and solid state bond.

Feedthrough pins for use in an implantable medical device have ends that are exposed to a recipient's tissue and/or body fluid. As such, feedthrough pins should be biocompatible. The need for biocompatibility has limited the choice of conductors and, in general, platinum is selected for the feedthrough pins. Alternatively, the feedthrough pin may be formed from stainless steel, titanium, Platinum Iridium, Gold, Nitinol, Palladium, or Molybdenum.

Additionally, feedthrough pins are electrically conductive so as to carry electrical signals between functional components outside of a hermetically sealed housing and electronics within the housing. As such, feedthrough pins should have a cross-sectional area that is sufficient to efficiently carry the electrical signals. This results in feedthrough pins having diameters that are large relative to the thicknesses of metallic coatings of the bonding pads.

As is well known, platinum, for example, is a dense and heavy material having a high melting point. These material properties, coupled with the sizing of the feedthrough pins relative to the pads/metallic coating, have necessitated the use of a few particular techniques to connect feedthrough pins to bonding pads, namely gap welding and soldering. Gap welding is the process of bonding metallic components together by placing both of the components in contact with a conductor that extends between the two components. In gap welding, the weld current flows from a first component through the connecting conductor before returning to a power supply via the second component. Soldering is a process in which two metallic components are joined together by melting and flowing a filler metal (solder) between the two components. The solder has a lower melting point than the two components. As such, it is apparent that conventional techniques used to join feedthrough pins to a bonding pad are implemented in manner that does not require melting or alteration of the state of the feedthrough pin or the bonding pad. One reason for this is that a conventional bonding process which would require the melting of a large feedthrough pin, particularly platinum, would result in the generation of a large amount of heat that would damage the bonding pad and/or the underlying PCB. As noted above, these requirements are unique to implantable medical devices and are generally not a concern in consumer electronic applications where all components are made as small as possible and there are no size/material mismatches.

In accordance with the examples presented herein, the use of the stud bumps on the surface of a bonding pad change the morphology of the bonding surface that enables the use of a bonding process that melts one or both of the feedthrough pin and the bonding pad (the metallic coating) without damaging the bonding pad or PCB. In particular, when a feedthrough pin is forced onto a bonding pad having stud bumps disposed thereon, the pressure of the contact points between the tops of the stud bumps and the pin will be highly increased relative to a flat bonding surface arrangement. The ultrasonic energy will also be highly increased at these points, effectively creating an amplification of the normal compression/ultrasonic effect at these contact points (relative to a flat bonding surface). A further effect of the increased pressure at the contact points will be greater deformation of the gold stud bump and the platinum feedthrough pin, thereby leading to the merging/fusing of the platinum of the feedthrough pin and the gold of the bonding pad (i.e., providing intimate contact between the elements and the mixing of the two surfaces into a continuous joint as they deform around each other).

As noted above, the bonding process that results in melting of the platinum feedthrough pin will generate an amount of force, energy, and heat would be sufficient to damage the bonding pad, wire, and/or the PCB. However, the inventors discovered that, by providing a sufficient number of gold stud bumps on the surface of the bonding pad, the energy from the bonding process may be dissipated without damaging the bonding pad and/or the PCB. In other words, the stud bumps are configured to be disposed on the surface of the bonding pad so as to provide a distributed medium that is sufficient to diffuse heat and energy from the joining process (i.e., the stud bumps collectively have a sufficient footprint and mass to function as a thermal energy sink in the case of heat based joining methods, and provides enough stud bump material to facilitate solid state joining in the case of mechanical bonding).

Conventionally, gold is generally not used as a heat sink. However, because the gold stud bumps collectively have a sufficient footprint and mass to function as a thermal energy sink, the stud bumps ensure that heat from the bonding process does not damage the PCB and the bonding pad. Stud bumps that are in contact with the feedthrough pin, as well as those that are not in contact with the pin, may operate as the heat sink.

In summary of the above, the energy sink in the form of the stud bumps is provided because the heat, force, and energy needed to melt the platinum wire to the gold pad is substantially more intense than the energy used in most wire bonding applications (i.e., higher energy is required to bond platinum to gold than is required to bond gold to gold). As such, the choice of materials used in this implantable medical device application, as well as the size of the feedthrough pin, creates the need for a unique bonding process that requires an energy sink. In general, the consumer electronics industry is moving to smaller and smaller wires, while implantable medical devices are limited by biocompatible and rare materials.

Certain conventional techniques for joining a feedthrough pin to a bonding pad, such as soldering, result in the introduction of potentially harmful materials into the implantable medical device. For example, soldering uses a material known as flux. The primary purposes of flux is to prevent oxidation of the filler material and to enable the filler material to flow easily on the working piece rather than forming beads as it would otherwise. Due to the corrosive and potentially harmful nature of most flux, all of the flux must be removed from the implantable component before implantation into a recipient. Flux is generally removed through a potentially time consuming and tedious washing/cleaning process. In accordance with embodiments of the present invention, no flux (or other potentially harmful materials) are needed for the stud bump bonding process. As such, the need to wash the implantable component prior to use within a recipient is eliminated as the reliability of the device is not compromised by the joining method (i.e., the joining method is non contaminating, therefore not requiring a cleaning operation).

Figure 5A:
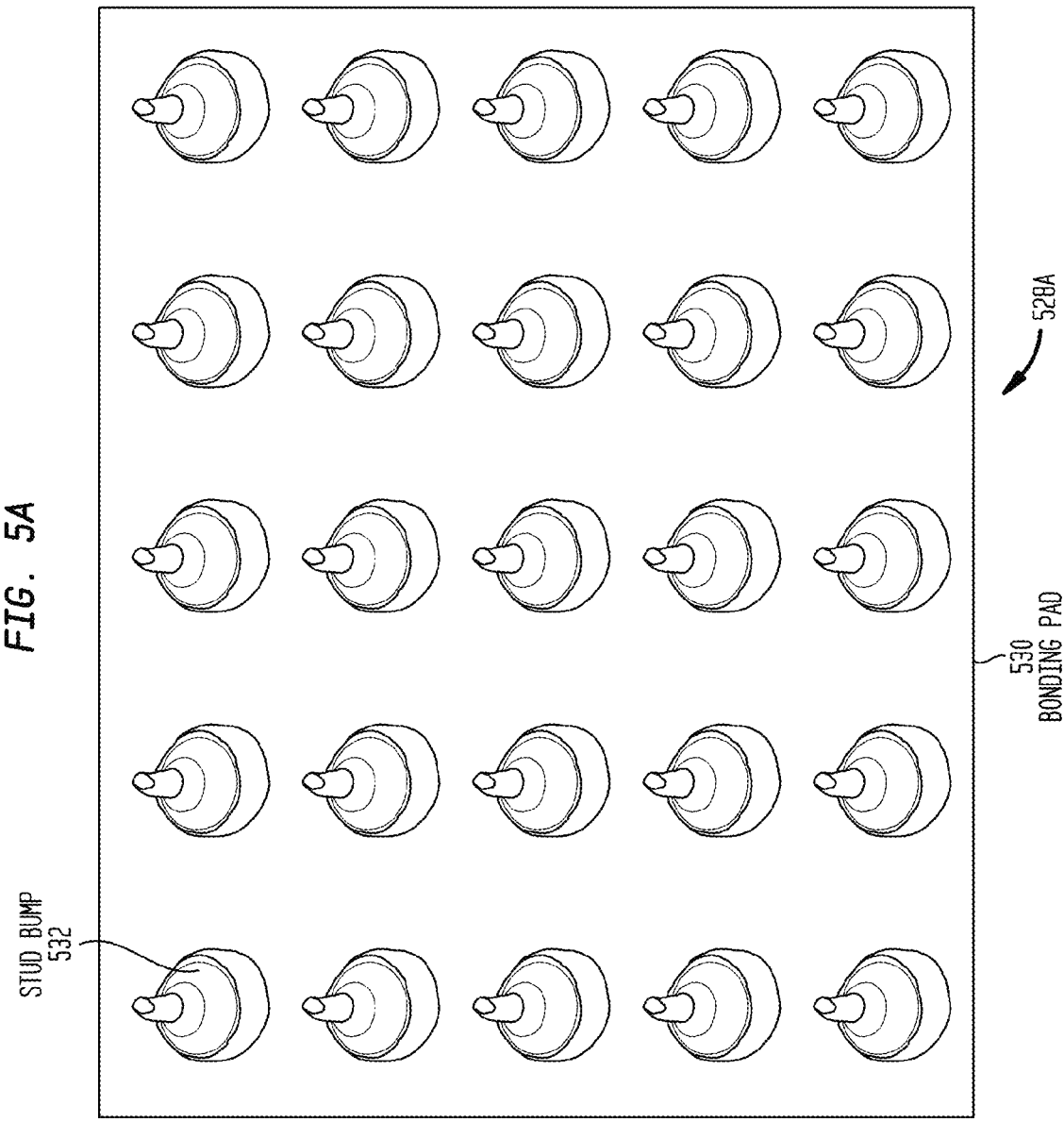

Also as noted above, embodiments of the present invention are directed to the use of a stud bump bonding process where a plurality of stud bumps are bonded to (formed on) a bonding pad. It is to be appreciated that different numbers of stud bumps may be bonded to a bonding pad in a number of different combinations. For example, FIG. 5A is a perspective view of one example arrangement 528A where twenty-five (25) stud bumps 532 are bonded to a bonding pad 530. As shown in FIG. 5A, the stud bumps 532 are evenly spaced on the surface of the bonding pad 530 in a 5×5 array.

FIG. 5B is a perspective view of another example arrangement 528B where sixteen (16) stud bumps 532 are bonded to a bonding pad 530. As shown in FIG. 5B, the stud bumps 532 are arranged in a 4×4 array at the center of the bonding pad 530. The bonding pad 530 includes a border area 534 to which no stud bumps 532 are bonded.

Figure 5C:
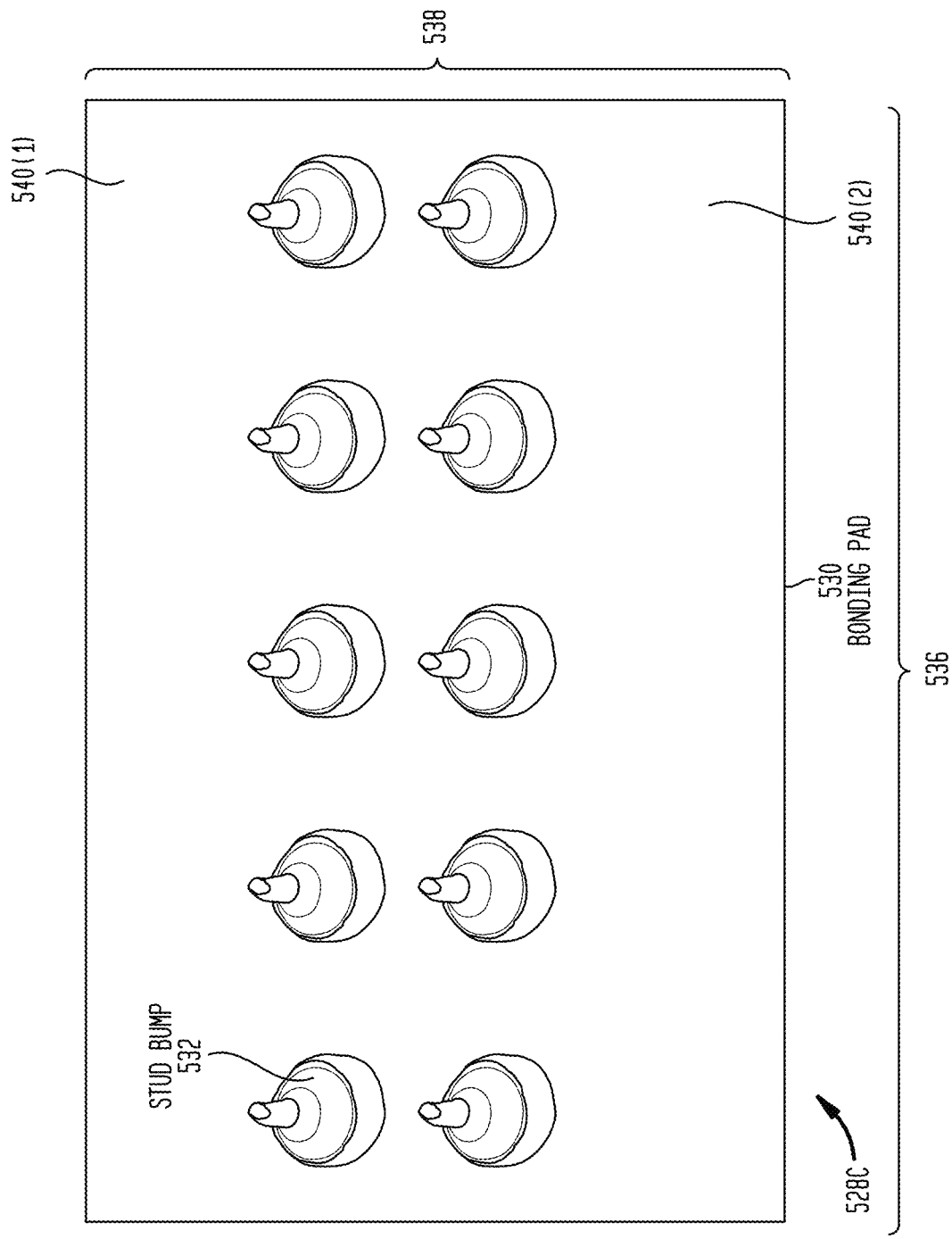

FIG. 5C is perspective view of another example arrangement 528C where ten (10) stud bumps 532 are bonded to a bonding pad 530. As shown in FIG. 5C, the stud bumps 532 are arranged in a 2×5 array that extends across the length 536 of the bonding pad 530. However, in this example, the array of stud bumps 532 does not extend across the entire width 538 of the bonding pad 530. Instead, the bonding pad 530 includes two elongate areas 540(1) and 540(2) to which no stud bumps 532 are bonded.

FIGS. 5A-5C illustrate arrangements where the stud bumps 532 are bonded to the bonding pad 530 at equal spaced, thereby forming a regular or organized arrangement of stud bumps. FIG. 5D is a perspective view of an example arrangement 528D where the stud bumps are bonded to the bonding pad in an irregular arrangement with, possibly, unequal spacing between one another.

It is to be appreciated that the arrangements of FIGS. 5A-5D are merely illustrative and other arrangements of stud bumps may be used in alternative embodiments of the present invention.

Additionally, it is to be appreciated that an apparatus used to form a stud bump may be very precise, there making the size, height, and geometry of stud bumps controllable. As such, the stud bumps 532 shown in FIGS. 5A-5D are merely illustrative and the stud bumps may have other shapes, sizes, etc. in alternative embodiments.

Figure 6:
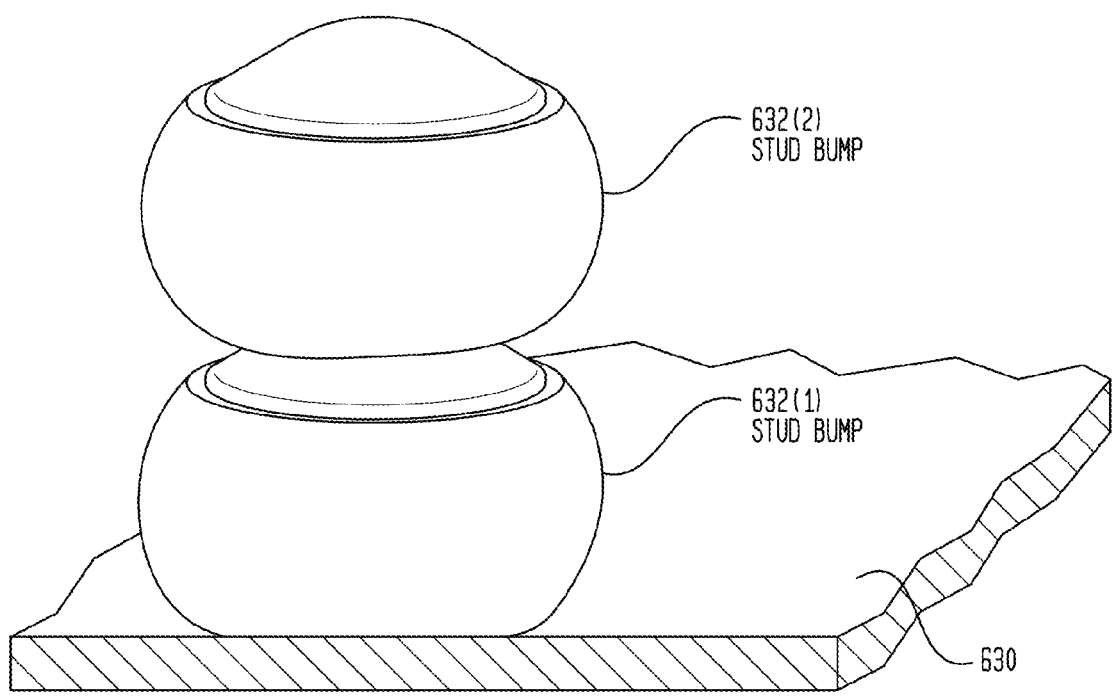
FIG. 6 is a perspective view of a stacked stud bump in accordance with embodiments of the present invention.

The above embodiments have generally been described with reference to the use of a single layer of stud bumps. However, is to be appreciated that alternative embodiments of the present invention may include multiple layers of stud bumps formed on a bonding pad. For example, FIG. 6 illustrates one example arrangement where two stud bumps 632(1) and 632(2) are disposed in a stacked arrangement on a bonding pad 630. In this example, stud bump 632(1) is first formed on the bonding pad 630. Subsequently, the second stud bump 632(2) is formed on top of the stud bump 632(1). Alternative arrangements may use three for more stacked stud bumps.

Figure 7:
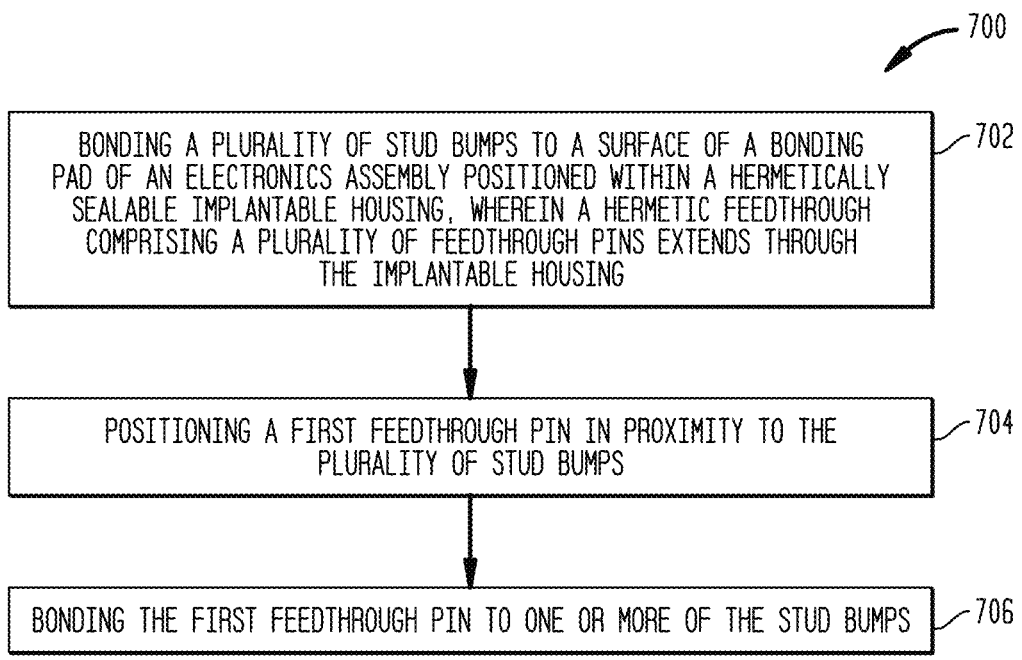
FIG. 7 is a high-level flowchart of a method in accordance with embodiments of the present invention.

FIG. 7 is a high-level flowchart of a method 700 in accordance with embodiments of the present invention. Method 700 begins at step 702 where a plurality of stud bumps are bonded to a surface of a bonding pad of an electronics assembly positioned within a hermetically sealable implantable housing. The housing includes a hermetic feedthrough that comprises a plurality of feedthrough pins that extend through the feedthrough. At 704, a first feedthrough pin is positioned in proximity to the plurality of stud bumps. At 706, the first feedthrough pin is bonded (e.g. ultrasonically, thermosonically, etc.) to one or more of the stud bumps.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method comprising:
  bonding a plurality of stud bumps to a surface of a bonding pad of an electronics assembly positioned within a hermetically sealable implantable housing, wherein a hermetic feedthrough comprising a plurality of feedthrough pins extends through the implantable housing;
  positioning a first feedthrough pin in proximity to the plurality of stud bumps; and
  bonding the first feedthrough pin to one or more of the stud bumps.

2. The method of claim 1, wherein bonding the plurality of stud bumps to the surface of the bonding pad comprises:
bonding a plurality of gold stud bumps to the bonding pad.

3. The method of claim 2, further comprising:
bonding the plurality of gold stud bumps to the bonding pad with a thermosonic wire ball bonding process.

4. The method of claim 3, wherein positioning the first feedthrough pin in proximity to the plurality of stud bumps comprises:
positioning a platinum feedthrough pin in proximity to the plurality of stud bumps.

5. The method of claim 1, wherein bonding the first feedthrough pin to the one or more stud bumps comprises:
ultrasonically bonding the first feedthrough pin to a plurality of stud bumps.

6. The method of claim 1, wherein bonding the first feedthrough pin to the one or more stud bumps comprises:
thermosonically bonding the first feedthrough pin to a plurality of stud bumps.

7. The method of claim 1, wherein bonding the plurality of stud bumps to the surface of the bonding pad comprises:
forming an array of stud bump elements on the surface of the bonding pad, wherein each stud bump element comprises two or more stacked stud bumps.

8. The method of claim 1, wherein bonding the plurality of stud bumps to the surface of the bonding pad comprises:
bonding the stud bumps on the surface of the bonding pad such that the stud bumps collectively function as a thermal energy sink during bonding of the first feedthrough pin to the one or more stud bumps.

9. The method of claim 1, further comprising:
hermetically sealing the implantable housing without first performing a washing process.

10. A method comprising:
bonding a plurality of stud bumps to a surface of a bonding pad;
positioning an elongate conductor adjacent to the plurality of stud bumps; and
laser welding the elongate conductor to one or more of the stud bumps, wherein the stud bumps collectively have a sufficient footprint and mass to function as a thermal energy sink during bonding of the elongate conductor to the one or more stud bumps.

11. The method of claim 10, wherein bonding the plurality of stud bumps to the surface of the bonding pad comprises:
bonding a plurality of gold stud bumps to the bonding pad.

12. The method of claim 11, further comprising:
thermosonically bonding the plurality of gold stud bumps to the bonding pad with a thermosonic wire ball bonding process.

13. The method of claim 10, wherein positioning the elongate conductor adjacent to the plurality of stud bumps comprises:
positioning a platinum wire adjacent to the plurality of stud bumps.

14. The method of claim 10, wherein bonding the plurality of stud bumps to the surface of the bonding pad comprises:
forming an array of stud bump elements on the surface of the bonding pad, wherein each stud bump element comprises two or more stacked stud bumps.

\* \* \* \* \*